United States Patent
Boileau et al.

(10) Patent No.: US 8,340,765 B2
(45) Date of Patent: Dec. 25, 2012

(54) SYSTEM AND METHOD FOR CONTROLLING VENTRICULAR PACING DURING AF BASED ON UNDERLYING VENTRICULAR RATES USING AN IMPLANTABLE MEDICAL DEVICE

(75) Inventors: Peter Boileau, Valencia, CA (US); Michael E. Benser, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 821 days.

(21) Appl. No.: 12/410,386

(22) Filed: Mar. 24, 2009

(65) Prior Publication Data
US 2010/0249862 A1    Sep. 30, 2010

(51) Int. Cl.
*A61N 1/36* (2006.01)
(52) U.S. Cl. .......................................... 607/14
(58) Field of Classification Search .................. 607/14, 607/9
See application file for complete search history.

(56) References Cited

U.S. PATENT DOCUMENTS

| | | | | |
|---|---|---|---|---|
| 5,480,413 A * | 1/1996 | Greenhut et al. | ............... | 607/14 |
| 6,129,746 A | 10/2000 | Levine et al. | | |
| 6,249,705 B1 | 6/2001 | Snell | | |
| 6,510,342 B1 | 1/2003 | Park et al. | | |
| 6,512,952 B2 | 1/2003 | Stahmann et al. | | |
| 6,519,493 B1 | 2/2003 | Florio et al. | | |
| 6,628,988 B2 | 9/2003 | Kramer et al. | | |
| 6,643,546 B2 | 11/2003 | Mathis et al. | | |
| 6,804,556 B1 | 10/2004 | Florio et al. | | |
| 6,990,374 B1 | 1/2006 | Florio et al. | | |
| 7,043,302 B1 | 5/2006 | Florio et al. | | |
| 7,103,411 B1 | 9/2006 | Park et al. | | |
| 7,120,490 B2 | 10/2006 | Chen et al. | | |
| 7,133,719 B1 | 11/2006 | Bornzin et al. | | |
| 7,142,915 B2 * | 11/2006 | Kramer et al. | ............... | 607/9 |
| 7,187,972 B1 | 3/2007 | Fain et al. | | |
| 7,212,860 B2 | 5/2007 | Stahmann et al. | | |
| 7,308,306 B1 * | 12/2007 | Park et al. | ............... | 607/9 |
| 2003/0130704 A1 | 7/2003 | Florio et al. | | |
| 2004/0215257 A1 | 10/2004 | Van Oort et al. | | |
| 2006/0224193 A1 | 10/2006 | Hess | | |

FOREIGN PATENT DOCUMENTS

WO    2004096341 A2    11/2004

OTHER PUBLICATIONS

Melenovsky et al. "Functional Impact of Rate Irregularity in Patients with Heart Failure and Atrial Fibrillation Receiving Cardiac Resynchronization Therapy." European Heart Journal (2005) 26, 705-711.

Noelker et al., "Dynamic Ventricular Overdrive during Atrial Fibrillation" Eurospace 2007; 9:iii45.

Noelker et al., "Dynamic Ventricular Overdrive during Atrial Fibrillation Decreases Heart Rate Irregularity and Increases Pacing." Eur Hart J 2008; 29:543.

* cited by examiner

*Primary Examiner* — Scott Getzow
*Assistant Examiner* — Amanda Patton

(57) ABSTRACT

Techniques are provided for controlling ventricular pacing during an episode of atrial fibrillation (AF) for use by a pacemaker, implantable cardioverter-defibrillator (ICD) or other implantable medical device. In one example, upon detection of AF, the underlying intrinsic ventricular rate of the patient is determined prior to delivering any ventricular pacing. Then, a ventricular pacing procedure—such as dynamic ventricular overdrive (DVO) pacing—is activated to reduce ventricular rate variability to mitigate the adverse effects of AF. The ventricular pacing procedure employed during AF is controlled based on a maximum ventricular rate set relative to the underlying intrinsic ventricular rate so as to keep an overall ventricular rate below the maximum rate.

20 Claims, 9 Drawing Sheets

SYSTEM AND METHOD FOR CONTROLLING VENTRICULAR PACING DURING AF BASED ON UNDERLYING VENTRICULAR RATES USING AN IMPLANTABLE MEDICAL DEVICE

FIELD OF THE INVENTION

The invention generally relates to implantable medical devices such as pacemakers and implantable cardioverter-defibrillators (ICDs) equipped to deliver cardiac resynchronization therapy (CRT), and in particular, to techniques for controlling ventricular pacing during atrial fibrillation (AF) using such devices.

BACKGROUND OF THE INVENTION

A pacemaker is an implantable medical device that recognizes various arrhythmias such as an abnormally slow heart rate (bradycardia) and delivers electrical pacing pulses to the heart in an effort to remedy the arrhythmias. An ICD is an implantable device that additionally recognizes ventricular tachycardia (VT) or ventricular fibrillation (VF) and delivers electrical shocks to terminate these tachyarrhythmias. CRT is a procedure for use by biventricular pacemakers or biventricular ICDs to resynchronize the ventricles for use within heart failure patients.

AF is a type of atrial tachycardia detectable by pacemakers and ICDs wherein the atria of the heart beat irregularly. AF is a common comorbidity in patients with CRT devices (i.e. within biventricular pacemakers and ICDs equipped to deliver CRT to resynchronize the ventricles.) Approximately 35% of CRT patients have AF. In the majority of those patients who also have intact atrioventricular (AV) nodal conduction, impulses from the atria during AF are often conducted to the ventricles at rapid and/or irregular intervals leading to high ventricular rates, ventricular rate irregularity and/or loss of ventricular pacing. High ventricular rates, especially with concomitant rate irregularity, compromise hemodynamic performance, exacerbate left ventricular dysfunction (see, e.g., Melenovsky et al. "Functional Impact of Rate Irregularity in Patients with Heart Failure and Atrial Fibrillation Receiving Cardiac Resynchronization Therapy" European Heart Journal (2005) 26, 705-711) and may predispose the patient to acutely decompensated heart failure. Additionally, reduced biventricular pacing decreases the benefit of CRT.

One option for responding to an episode of AF is to deliver cardioversion shocks to terminate the episode, i.e. strong electrical shocks can be delivered to the atria in an attempt to revert the atria from fibrillation to a normal sinus rhythm. Although cardioversion can be effective in terminating an individual episode of AF, in many cases fibrillation eventually resumes, requiring another round of shocks. Repeated shocks are quite painful to the patient and can deplete battery resources of the implanted device. Because AF is not usually immediately life threatening, painful shocks for its treatment may be perceived by patients as worse than the disease itself and therefore not tolerated.

As some patients have hundreds of AF episodes annually, it is instead desirable to employ ventricular pacing techniques for pacing the heart during AF so as to mitigate the adverse effects of AF rather than terminating the episode using cardioversion shocks. In particular, it is desirable to pace the ventricles so as to stabilize the ventricular rate during AF. A particularly effective technique for controlling ventricular overdrive pacing during AF is dynamic ventricular overdrive (DVO), which is described in U.S. Pat. No. 7,308,306 to Park et al. DVO is also discussed in U.S. patent application Ser. No. 11/929,719, of Bornzin et al., filed on Oct. 30, 2007, entitled "Systems and Methods for Paired/Coupled Pacing and Dynamic Overdrive/Underdrive Pacing." Briefly, with DVO, the ventricles are paced at an overdrive pacing rate selected to permit the detection of the least some intrinsic ventricular pulses, and then the overdrive pacing rate is dynamically adjusted based on the detected intrinsic ventricular pulses. In one example, an increase in the ventricular overdrive rate is performed only in response to detection of at least two intrinsic ventricular beats within a predetermined search period. If at least two intrinsic ventricular beats are not detected within the search period, the overdrive pacing rate is decreased.

Another useful ventricular pacing technique is the floating base rate pacing technique set forth in U.S. Pat. No. 7,187,972 to Fain et al. Briefly, pacing techniques are described therein for maintaining a high target percentage of biventricular paced beats during AF, wherein the ventricles are paced in accordance with a floating mode-switch base rate (MSBR) during AF (or, more generally, during any "non-atrial tracking ventricular pacing mode" following a mode-switch from an "atrial tracking mode.") Monitoring is performed to determine whether biventricular pacing in accordance with the MSBR satisfies a minimum acceptable pacing criterion (MAPC). The MSBR is increased and pacing is performed in accordance with the increased MSBR, when the MAPC is not satisfied. The MSBR is periodically decreased and biventricular pacing is performed in accordance with the decreased MSBR when the MAPC is satisfied. Herein, the technique of U.S. Pat. No. 7,187,972 and related techniques are referred to as Floating Base Rate (FBR) pacing techniques. [It may also be referred to as the Fain/Ostrow pacing technique.] FBR pacing can be used in heart failure patients receiving CRT, which seeks to resynchronize the ventricles while achieving a high percentage of paced ventricular beats.

Hence, various ventricular pacing therapies have been developed for controlling pacing of the ventricles during AF to mitigate the effects of AF, including procedures adapted for use with heart failure patients receiving CRT. As noted, some of these techniques seek to achieve a high percentage of paced ventricular beats. In some instances, this is performed without regard to the resulting mean ventricular rate, which, in at least some cases, can become elevated. Elevated ventricular rates, though, are seen by clinicians as disadvantageous, particularly within heart failure patients.

Accordingly, it would be desirable to provide techniques for controlling ventricular pacing during AF so as to reduce or minimize mean ventricular rates within at least some patients, and it is to this end that the invention is generally directed.

SUMMARY OF THE INVENTION

In accordance with an exemplary embodiment of the invention, a method is provided for controlling pacing during AF for use by an implantable medical device such as a pacemaker or ICD. Briefly, a maximum ventricular rate increase ($VR_{MAX-INCREASE}$) or rate "delta" is input, which may be a clinician-specified value pre-programmed into the device or may be determined by the device. This value may be set, for example, in the range of 0 to 40 pulses per minute (ppm.) The implantable device detects AF and then determines the underlying intrinsic ventricular rate ($VR_{UNDERLYING}$) of the patient during AF. Ventricular pacing therapy is delivered by the device during AF at a ventricular pacing rate (VR) not exceeding a maximum ventricular rate ($VR_{MAX}$) set based, at least in part, on the underlying intrinsic ventricular rate ($VR_{UNDERLYING}$) and the maximum rate increase ($VR_{MAX-INCREASE}$).

For example, $VR_{MAX}$ may be set to $VR_{UNDERLYING}$ plus $VR_{MAX-INCREASE}$. By controlling ventricular pacing during AF based, in part, on the underlying intrinsic ventricular rate ($VR_{UNDERLYING}$), the mean ventricular rate can be reduced or minimized in many cases, while also achieving ventricular rate stabilization. Preferably, ventricular pacing therapy during AF is controlled to maintain an overall ventricular rate—representative of both paced beats and intrinsic beats—below the maximum rate. In an illustrative example, upon detection of an episode of AF, ventricular pacing therapy is temporarily delayed to allow the device to detect the intrinsic ventricular rate, which is used as $VR_{UNDERLYING}$ to initially set $VR_{MAX}$. For example, during the first five to ten seconds of AF, the device withholds any ventricular pacing in order to detect $VR_{UNDERLYING}$ and set $VR_{MAX}$. Then, ventricular pacing is activated and controlled so as to maintain the overall ventricular rate below $VR_{MAX}$.

Depending upon the particular ventricular pacing procedure employed during AF, control parameters are automatically and adaptively adjusted to ensure the ventricular rate does not exceed $VR_{MAX}$ during AF. For example, if DVO pacing is delivered, the device selectively adjusts one or more DVO control parameters such as (1) a predetermined maximum allowed DVO pacing rate, (preferably set to a value that is the lesser of a user-programmed value and $VR_{MAX}$ (2) the DVO slope, (3) the number of overdrive cycles before a rate reduction (i.e. the DVO dwell time) and (4) the number of intrinsic beats required to trigger a rate increase. Preferably, these parameters are adjusted sequentially—and in that particular order—to control DVO to reduce VR. If FBR pacing is additionally or alternatively employed, the device selectively adjusts an FBR control parameter specifying the target proportion of paced to sensed beats.

Preferably, the current value for $VR_{UNDERLYING}$ is updated during the episode of AF. In one example, any on-going ventricular pacing during AF is periodically suspended to allow for detection of intrinsic ventricular beats for use in resetting $VR_{MAX}$. Such periodic suspensions of pacing can be, e.g., in the range of every thirty seconds to every six hours. The frequency at which suspensions are performed may be adjusted based on the relative stability of $VR_{UNDERLYING}$ as determined based on rate variance measurements, the time of day or the level of activity. In one particular example, after one week (assuming the episode of AF lasts that long), the frequency of periodic suspensions is reduced if $VR_{UNDERLYING}$ is found to be relatively stable based on rate variance. Alternatively, rather than temporarily suspending pacing to update $VR_{UNDERLYING}$, the device temporarily switches to a ventricular-triggered pacing mode (i.e. VVT pacing.) Intrinsic ventricular events detected during VVT are used to update the value for $VR_{UNDERLYING}$. In the various illustrative embodiments, by controlling ventricular pacing parameters during AF based on a $VR_{MAX}$ value derived from $VR_{UNDERLYING}$, the mean ventricular rate during an episode of AF can typically be reduced, minimized or otherwise controlled. This is particularly advantageous within heart failure patients where a high ventricular rate may be problematic.

Method, system and apparatus embodiments of the invention are described herein.

BRIEF DESCRIPTION OF THE DRAWINGS

The above and further features, advantages and benefits of the invention will be apparent upon consideration of the present description taken in conjunction with the accompanying drawings, in which.

DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators are used to refer to like parts or elements throughout.

Overview of Implantable Medical System

Figure 1:
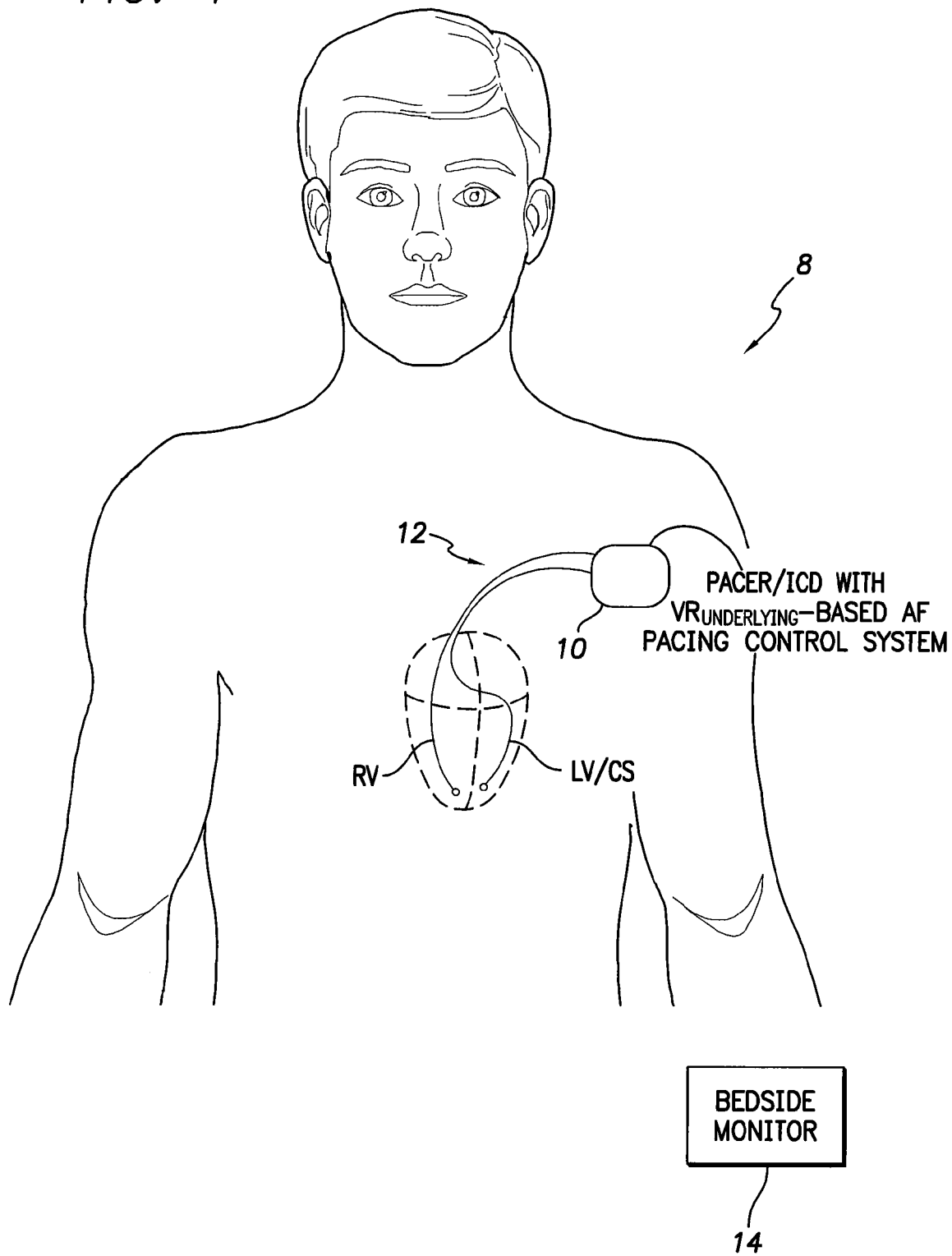
FIG. 1 illustrates pertinent components of an implantable medical system having a pacer/ICD equipped with $VR_{UNDERLYING}$-based AF pacing rate control system operative to control the ventricular pacing rate during AF based on $VR_{UNDERLYING}$.
Figure 8:
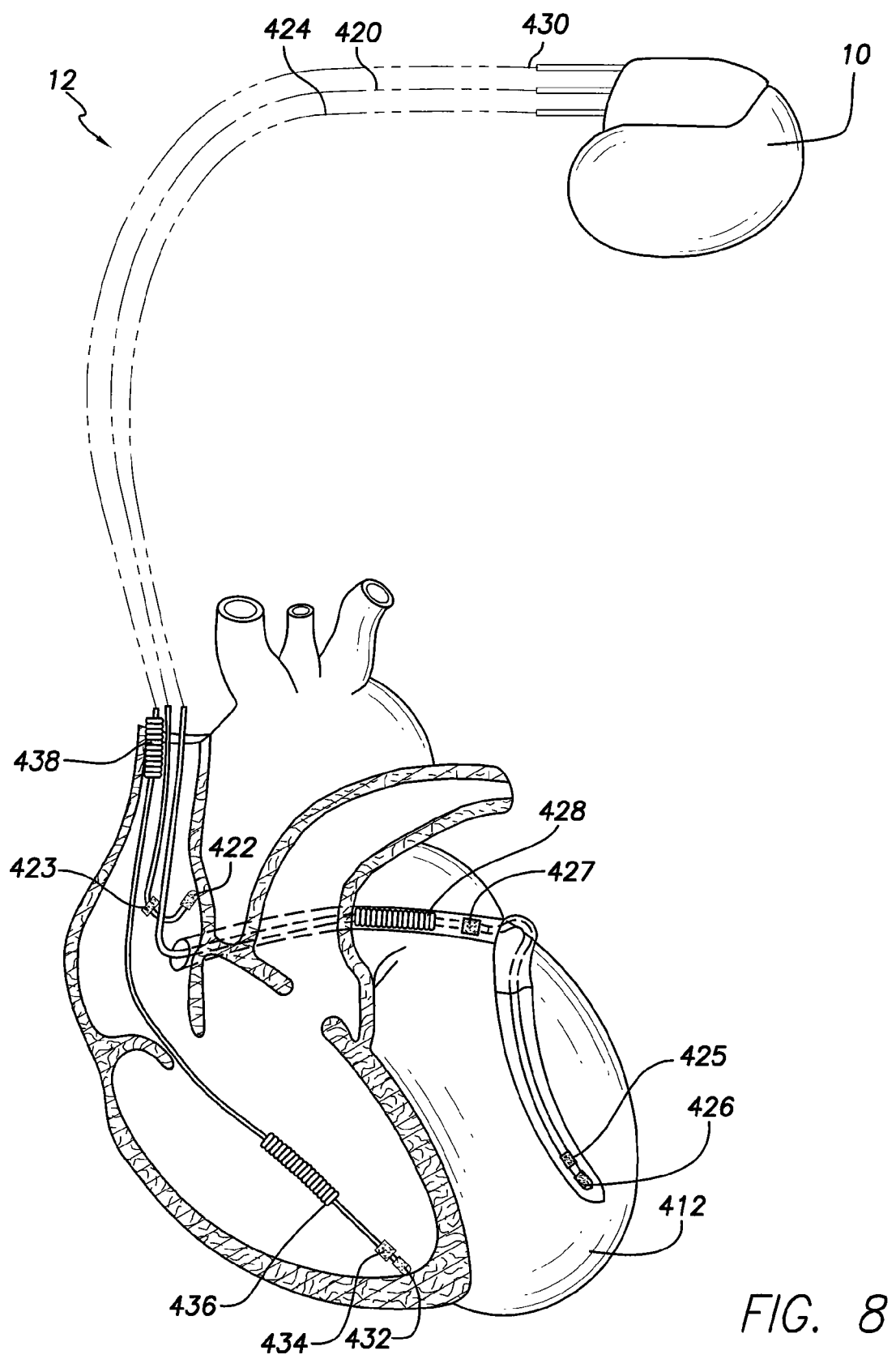
FIG. 8 is a simplified, partly cutaway view, illustrating the pacer/ICD of FIG. 1 along with a more complete set of exemplary leads implanted in the heart of a patient.

FIG. 1 illustrates an implantable medical system 8 capable of controlling ventricular pacing during an episode of AF within the heart of a patient based on an underlying intrinsic ventricular rate ($VR_{UNDERLYING}$.) To this end, a pacer/ICD 10 (or other suitable implantable medical device) uses one or more cardiac pacing/sensing leads 12 to detect a set of intracardiac electrogram (IEGM) signals from which intrinsic atrial and ventricular rates can be determined. The pacing/sensing leads are also employed to deliver cardiac pacing therapy, including, e.g., VVT, DVO and FBR pacing. In FIG. 1, only two exemplary leads are shown: an RV lead and an LV lead implanted via the coronary sinus (CS). A more complete set of leads is illustrated in FIG. 8.

The pacer/ICD includes a $VR_{UNDERLYING}$-based AF pacing control system operative to control delivery of ventricular pacing to the heart of the patient during AF at a ventricular rate not exceeding a maximum rate ($VR_{MAX}$) set based on the underlying intrinsic ventricular rate ($VR_{UNDERLYING}$.) $VR_{UNDERLYING}$ is determined by the pacer/ICD based on IEGM signals sensed using the leads, in conjunction with a maximum rate increase ($VR_{MAX\text{-}INCREASE}$) or rate delta programmed into the device by a clinician or otherwise determined. Exemplary techniques for detecting $VR_{UNDERLYING}$ and for controlling ventricular pacing therapy based on $VR_{UNDERLYING}$ will be described in detail below.

Diagnostic information pertaining to episodes of AF and to specific ventricular pacing control parameters employed by the pacer/ICD during AF may be stored within the pacer/ICD for subsequent transmission to an external programmer (not shown in FIG. 1) for review by a clinician or may be transmitted to a bedside monitor 14 (if one is provided) for immediate forwarding to the clinician via a communication network. Warning signals may be generated using the bedside monitor (or via an implanted warning device, not shown) for notifying the patient of any concerns, such as warning of any significant increase in the frequency or duration of episodes of AF.

Note that external programmers are typically used only during follow-up sessions with the patient wherein a clinician downloads information from the implanted device, reviews the information and then adjusts the control parameters of the implanted device, if needed, via the programmer. Bedside monitors typically download information more frequently, such as once per evening, and can be equipped to relay the most pertinent information to the appropriate clinician via a communication network. In any case, the clinician may then prescribe any appropriate therapies to address the episodes of AF or to address other medical concerns. The clinician may also adjust the operation of the pacer/ICD to activate, deactivate or otherwise control any ventricular pacing therapies that are automatically applied.

Note that the bedside monitor may be directly networked with a centralized computing system, such as the House-Call™ system or the Merlin@home/Merlin.Net systems of St. Jude Medical, for immediately notifying the clinician of any significant deterioration in the heart of the patient, as indicated, e.g., by an increase in the duration or frequency of episodes of AF. Networking techniques for use with implantable medical systems are set forth, for example, in U.S. Pat. No. 6,249,705 to Snell, entitled "Distributed Network System for Use with Implantable Medical Devices."

Preferably, the pacer/ICD is also equipped to deliver CRT to the heart of the patient, particularly if the patient has heart failure. Briefly, CRT seeks to normalize asynchronous cardiac electrical activation and resultant asynchronous contractions associated with heart failure by delivering pacing stimuli to both ventricles. The stimuli are timed so as to improve overall cardiac function. This may have the additional beneficial effect of reducing the susceptibility to life-threatening tachyarrhythmias. CRT and related therapies are discussed in, for example, U.S. Pat. No. 6,643,546 to Mathis, et al., entitled "Multi-Electrode Apparatus and Method for Treatment of Congestive Heart Failure"; U.S. Pat. No. 6,628,988 to Kramer, et al., entitled "Apparatus and Method for Reversal of Myocardial Remodeling with Electrical Stimulation"; and U.S. Pat. No. 6,512,952 to Stahmann, et al., entitled "Method and Apparatus for Maintaining Synchronized Pacing".

The pacer/ICD also performs numerous other functions and operations, such as monitoring the heart for VF and delivering defibrillation shocks in response thereto.

Hence, FIG. 1 provides an overview of an implantable system capable detecting an underlying intrinsic ventricular rate and controlling ventricular pacing therapy during AF based on the underlying rate, generating any appropriate warning/notification signals, and recording suitable diagnostics. Embodiments may be implemented that do not necessarily perform all of these functions. For example, embodiments may be implemented that provide only for control of ventricular pacing but not for generation of warning signals. Some implementations may not employ a bedside monitor. These are just a few examples. No attempt is made herein to describe all possible combinations of internal or external components that may be provided in accordance with the general principles of the invention. In addition, note that the particular sizes, shapes and locations of the implanted components shown in FIG. 1 are merely illustrative.

Overview of Techniques for Controlling Ventricular Pacing During AF

Figure 2:
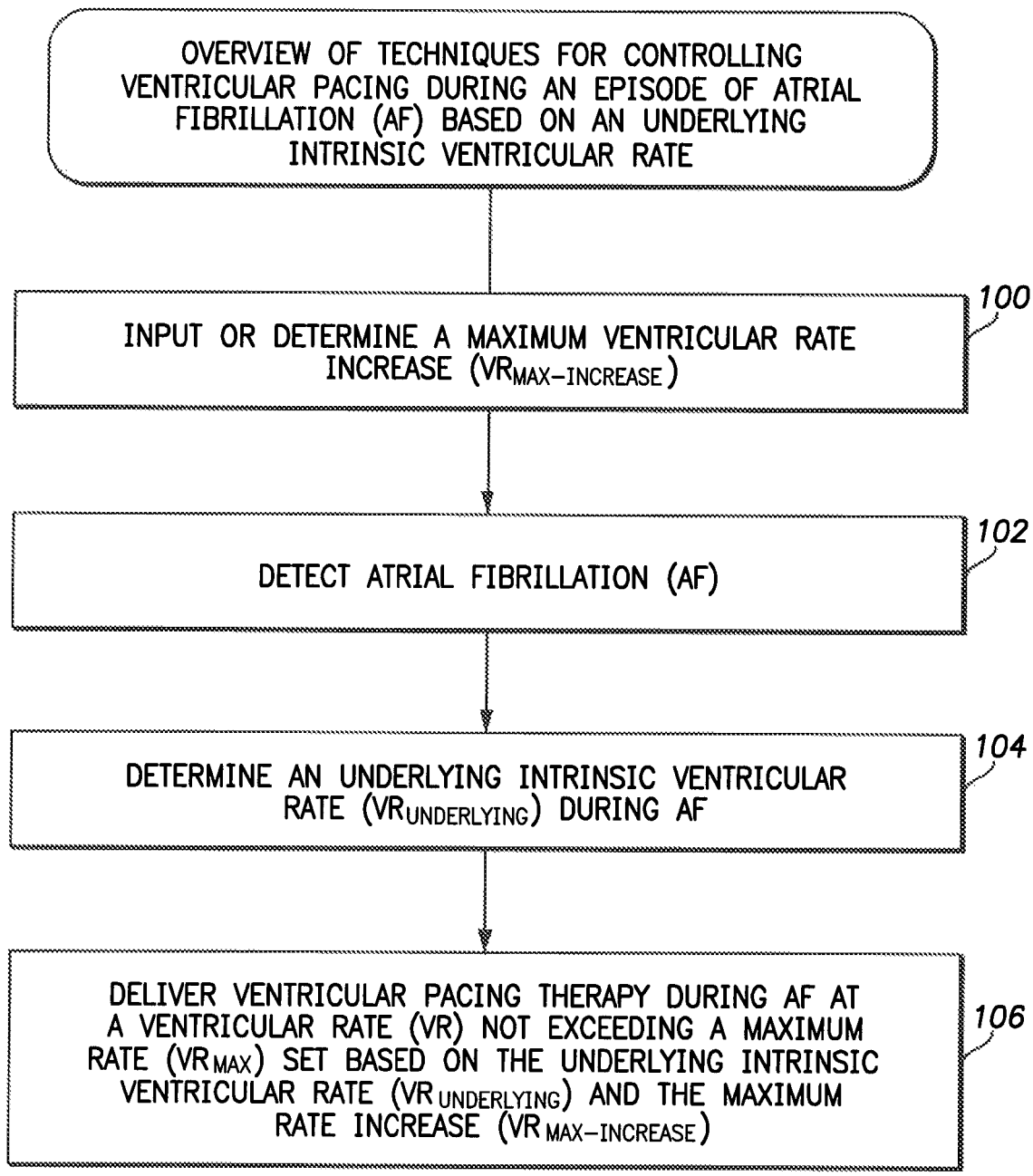
FIG. 2 is a flow diagram providing an overview of a technique for controlling ventricular pacing during AF based on $VR_{UNDERLYING}$, which may be performed by the system of FIG. 1.

FIG. 2 broadly summarizes techniques for controlling ventricular pacing during AF based on an underlying intrinsic ventricular rate, which may be performed by the pacer/ICD of FIG. 1 or by other suitably equipped implantable devices or systems. Beginning at step 100, the pacer/ICD inputs or otherwise determines a maximum ventricular rate increase ($VR_{MAX\text{-}INCREASE}$) or rate delta, which may be programmed into the pacer/ICD by a clinician during a post-implant programming session. The rate increase may be, for example, programmed within the range of 0 to 40 ppm. In other examples, $VR_{MAX\text{-}INCREASE}$ is not necessarily a programmed value but is instead determined by the device based, e.g., on a measured degree of underlying heart irregularity. (Any determination of underlying heart rate irregularity would preferably be made after detection of AF.) At step 102, the pacer/ICD monitors atrial IEGM signals to detect an episode of AF. This may be achieved by comparing the atrial rate with a predetermined AF detection threshold (AFDT). If the atrial rate exceeds the AFDT, then AF is presumed. Alternatively, the pacer/ICD may examine the morphology of the atrial IEGM to detect signal morphologies indicative of AF. At step 104, the pacer/ICD determines the underlying intrinsic ventricular rate ($VR_{UNDERLYING}$) during AF. In one example, the pacer/ICD determines an initial value for $VR_{UNDERLYING}$ at the onset of AF before ventricular pacing is initiated. Thereafter, $VR_{UNDERLYING}$ is preferably updated throughout the episode of AF. Various exemplary techniques will be described below to update the value of $VR_{UNDERLYING}$ wherein, for example, ventricular pacing is temporarily suspended.

At step 106, the pacer/ICD delivers ventricular pacing therapy during the episode of AF at a ventricular rate (VR) not exceeding a maximum rate ($VR_{MAX}$) set based on $VR_{UNDERLYING}$ and $VR_{MAX\text{-}INCREASE}$. As already noted, $VR_{MAX}$ may be set to $VR_{UNDERLYING}+VR_{MAX\text{-}INCREASE}$. So, in an example where the clinician has specified a $VR_{MAX\text{-}INCREASE}$ of 10 bpm, and where the underlying intrinsic VR rate is 75 bpm, the pacer/ICD delivers ventricular pacing to the ventricles at a rate not exceeding 85 bpm. Also, as noted above, ventricular pacing is preferably controlled to maintain an overall ventricular rate—representative of both paced beats and intrinsic beats—below $VR_{MAX}$. The specific manner by which the pacer/ICD controls the ventricular rate to not exceed $VR_{MAX}$ depends on the particular ventricular pacing procedure employed during AF. Examples are described below with reference to FIG. 7 for DVO and for FBR pacing.

Figure 3:
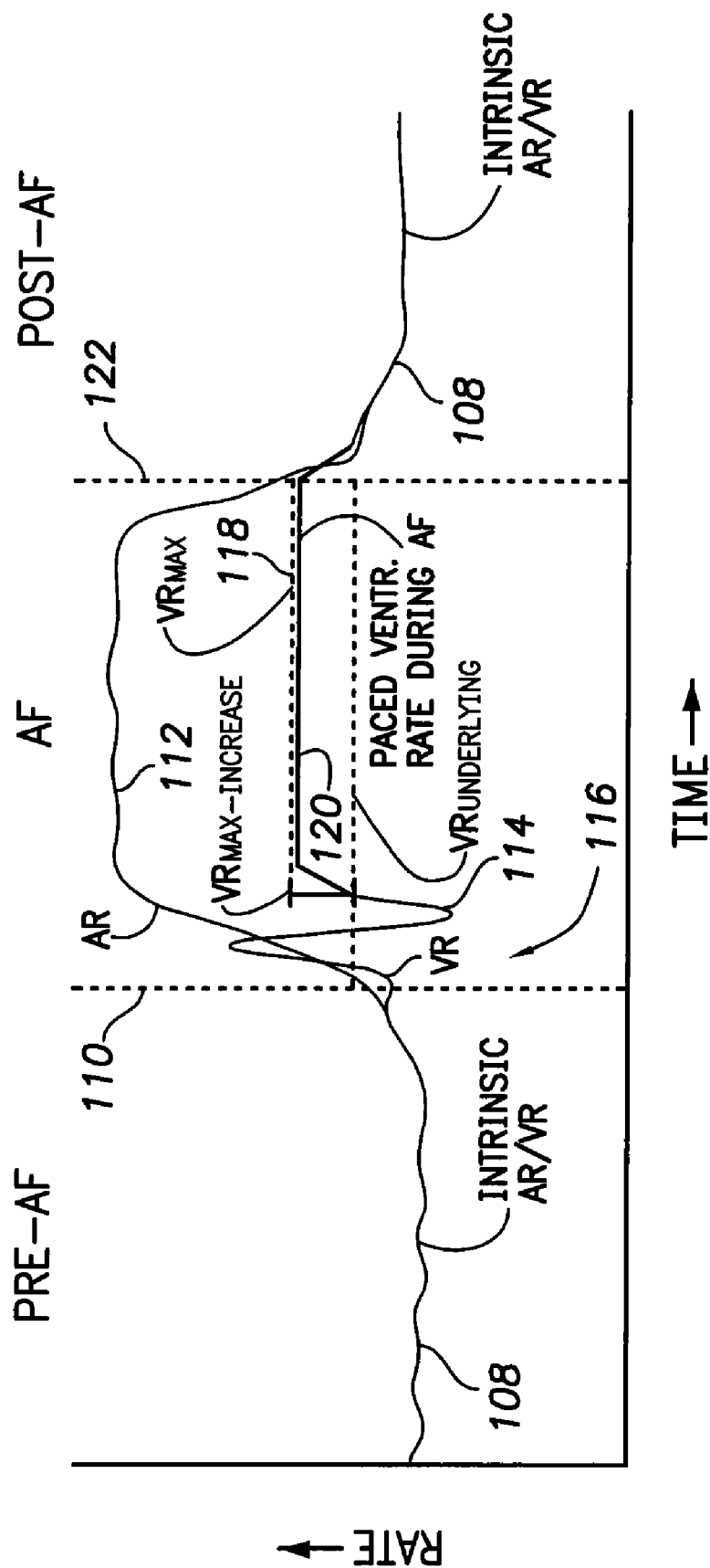
FIG. 3 is a graph illustrating exemplary pacing rates and intrinsic rates, and particularly illustrating the use of $VR_{MAX-INCREASE}$ to set $VR_{MAX}$ based on $VR_{UNDERLYING}$ during AF, in accordance with one example of the general technique of FIG. 2.

FIG. 3 graphically illustrates an example of the general technique of FIG. 2 wherein $VR_{UNDERLYING}$ is initially determined upon the onset of an episode of AF. In this example, prior to AF, the intrinsic atrial and ventricular rates 108 are the same and no pacing is delivered. Upon the onset of AF at time 110, the atrial rate 112 increases rapidly, whereas the intrinsic ventricular rate 114 remains comparatively low but begins to become quite unstable. The pacer/ICD tracks the intrinsic ventricular rate by detecting intrinsic ventricular beats during an initial period or interval 116 of five to ten seconds at the beginning of the episode and then measuring the intervals between the intrinsic ventricular beats. These intervals can be averaged to yield an average or mean value for the intrinsic ventricular rate despite the rate instability. This average value for the intrinsic ventricular rate is used as the initial value for $VR_{UNDERLYING}$ for setting an initial value for $VR_{MAX}$ 118 based on $VR_{MAX-INCREASE}$. Ventricular pacing is then activated and delivered at a VR rate 120 at or below $VR_{MAX}$ 118. This achieves rate stabilization while also keeping the paced ventricular rate relatively low.

The ventricular pacing procedure may employ DVO, FBR pacing or other pacing protocols. For clarity and simplicity, a constant ventricular pacing rate 120 is illustrated, without any of the occasional ventricular pacing rate variations that might be performed during DVO or FBR pacing. The particular manner by which VR is held below $VR_{MAX}$ during AF depends upon the particular ventricular pacing procedure and examples are discussed below. As noted, ventricular pacing can be temporarily and periodically suspended during AF or switched to VVT to update the value for $VR_{UNDERLYING}$. In FIG. 3, for clarity and simplicity, any such temporary suspensions of pacing are not shown. Once the episode of AF terminates at time 122—either naturally or due to therapy—the atrial and ventricular rates return to non-AF rate 108.

In this manner, using the techniques of FIGS. 2-3, the ventricular pacing rate during AF is held below a maximum rate ($VR_{MAX}$) controlled based on the $VR_{UNDERLYING}$ and the clinician-specified maximum permissible rate increase $VR_{MAX-INCREASE}$. In practice, $VR_{MAX-INCREASE}$ is set fairly low so as to reduce the mean ventricular rate during AF (at least as compared to alternative techniques wherein a fixed maximum ventricular rate is instead specified that might result in ventricular rates higher than $VR_{MAX}$ during AF.) As such, the technique of FIGS. 2-3 provides an effective method for allowing the pacer/ICD to achieve a relatively low mean ventricular rate during AF while also achieving ventricular rate stability.

Exemplary Techniques for Controlling Ventricular Pacing During AF

Figure 4:
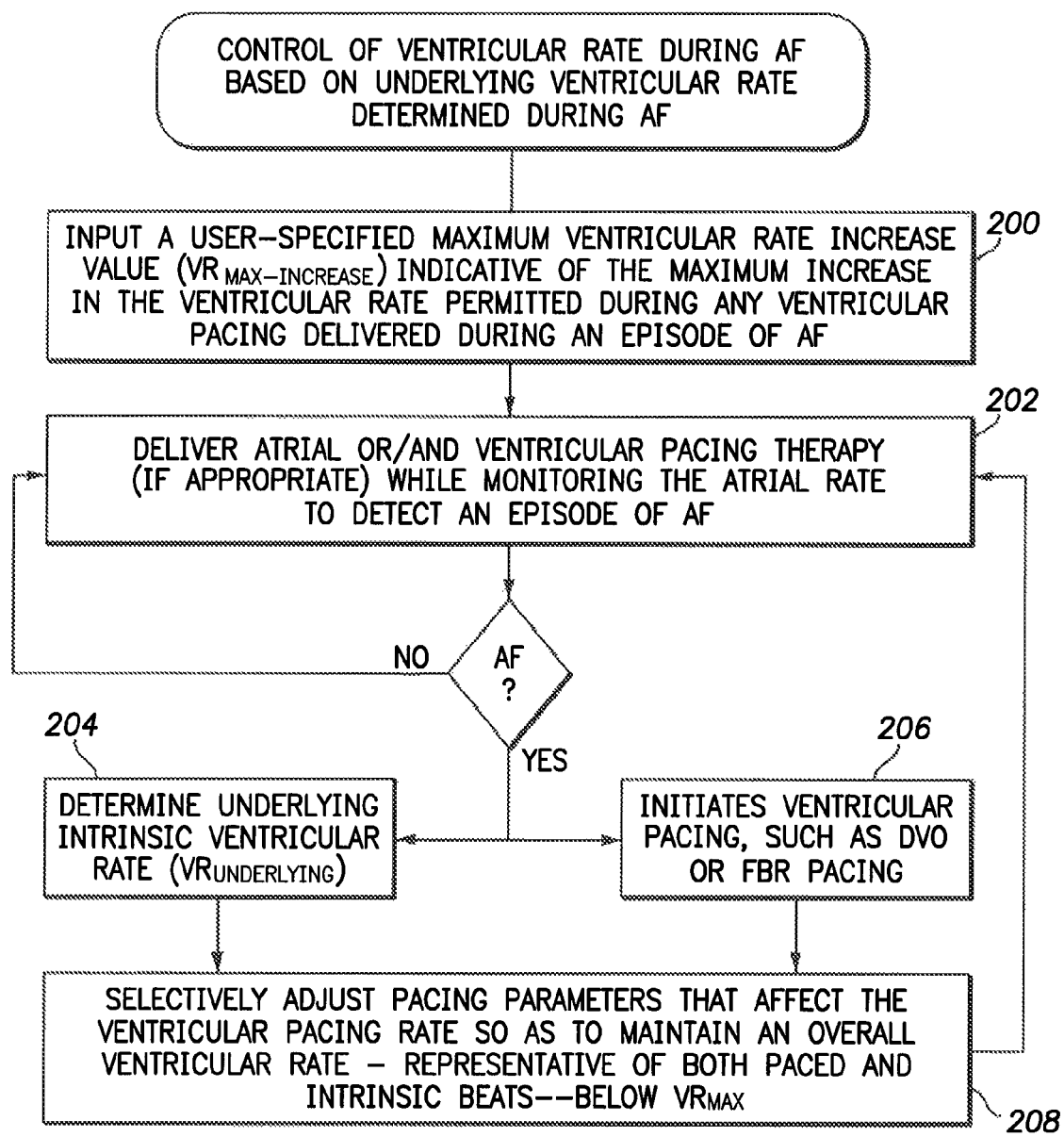
FIG. 4 is an illustrative procedure for controlling the ventricular rate during AF in accordance with the general technique of FIG. 2, wherein $VR_{UNDERLYING}$ is determined and exploited during an episode of AF.

FIG. 4 illustrates an exemplary technique of the general method FIG. 2, wherein $VR_{UNDERLYING}$ is determined during AF for use in controlling ventricular pacing. Beginning at step 200, the pacer/ICD inputs from memory the user-specified maximum ventricular rate increase value ($VR_{MAX-INCREASE}$) indicative of the maximum increase in ventricular rate permitted during any ventricular pacing delivered during an episode of AF. As noted, this value can be initially programmed by a clinician using an external device programmer. At step 202, the pacer/ICD delivers pacing to the heart of the patient using a selected pacing procedure, protocol or regime, such as dynamic atrial overdrive (DAO) or other suitable AF suppression procedures while monitoring the atrial rate to detect AF. [DAO is discussed in, for example, U.S. Pat. No. 6,519,493 to Florio et al., entitled "Methods and Apparatus for Overdrive Pacing Heart Tissue Using an Implantable Cardiac Stimulation Device." With DAO, the overdrive atrial pacing rate is controlled to remain generally uniform and, in the absence of a tachycardia, is adjusted upwardly or downwardly only occasionally in response to breakthrough sinus beats.] In other examples, no pacing is delivered prior to detection of AF.

Upon detection of AF, the pacer/ICD determines the underlying intrinsic ventricular rate ($VR_{UNDERLYING}$) at step 204 and initiates a ventricular pacing procedure, such as DVO or FBR pacing, at step 206. In some examples, ventricular pacing is immediately activated but then periodically suspended (or switched to VVT) to permit detection of $VR_{UNDERLYING}$. In other examples, $VR_{UNDERLYING}$ is detected before ventricular pacing is activated. Even in those examples, ventricular pacing is thereafter periodically suspended (or switched to VVT) to permit updating the value of $VR_{UNDERLYING}$. Hence, for generality, steps 204 and 206 are shown side-by-side in the figure.

More specifically, at step 204, the pacer/ICD detects $VR_{UNDERLYING}$ by: (1) delaying activation of ventricular pacing until the intrinsic ventricular rate can be detected; (2) periodically suspending any on-going ventricular pacing; (3) periodically switching to VVT pacing; or by implementing any other technique sufficient to permit $VR_{UNDERLYING}$ to be detected or determined. Technique (1) is discussed in greater detail below with reference to FIG. 5. Techniques (2) and (3) are discussed in greater detail below with reference to FIG. 6. At step 208, the pacer/ICD delivers ventricular pacing therapy while selectively adjusting pacing parameters that affect the ventricular pacing rate so as to maintain an overall ventricular rate—representative of both paced and intrinsic beats—below a maximum permissible rate ($VR_{MAX}$) set equal to the underlying intrinsic ventricular rate ($VR_{UNDERLYING}$) and the maximum rate increase ($VR_{MAX-INCREASE}$). As noted, the specific manner in which the pacer/ICD controls the ventricular rate to not exceed $VR_{MAX}$ depends on the particular ventricular pacing procedure employed during AF. Exemplary techniques for controlling DVO and FBR pacing are discussed in greater detail below with reference to FIG. 7.

Figure 5:
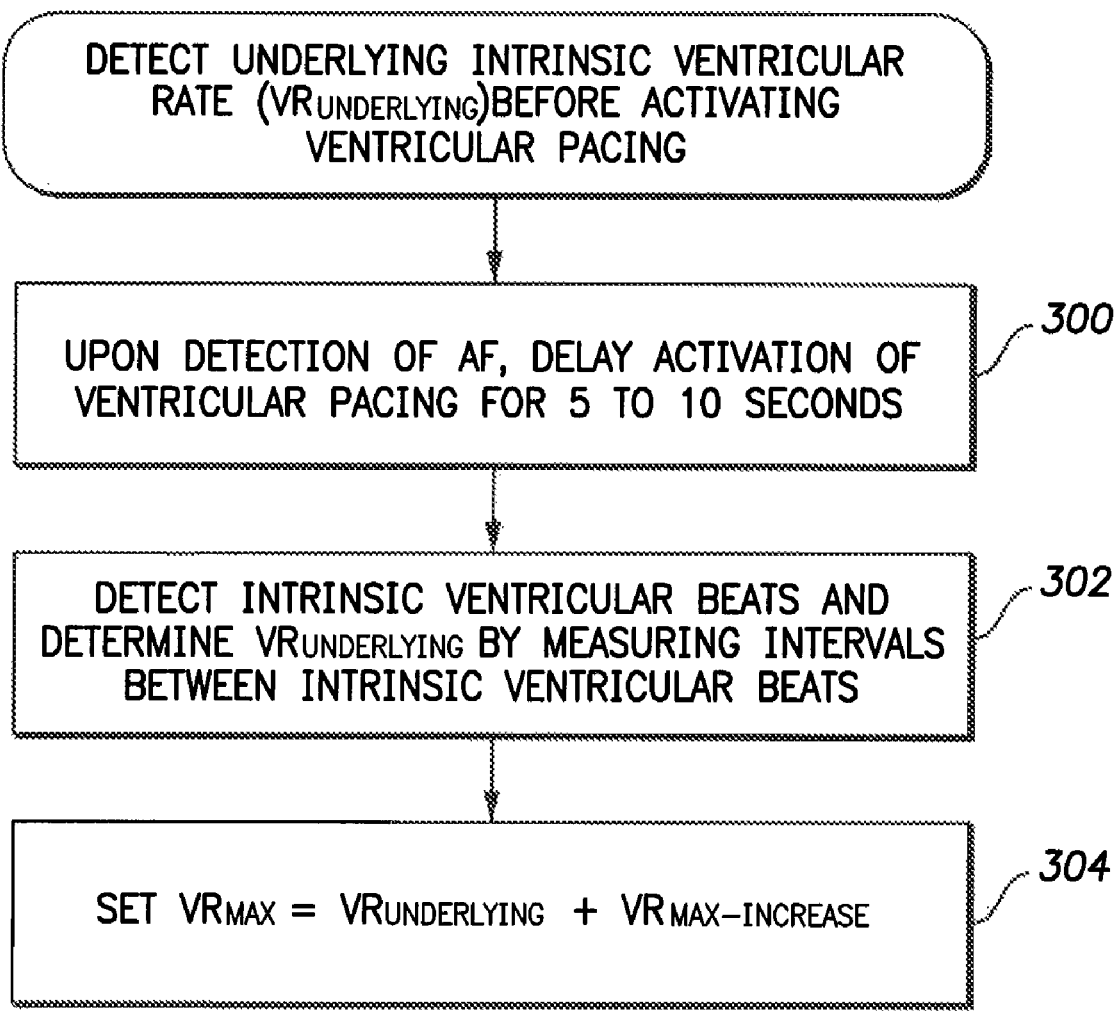
FIG. 5 illustrates an exemplary technique for detecting $VR_{UNDERLYING}$ for use with the procedure of FIG. 4, wherein the activation of ventricular pacing during AF is delayed to allow for an initial detection of $VR_{UNDERLYING}$.

FIG. 5 illustrates exemplary techniques for use at step 204 of FIG. 4 for determining $VR_{UNDERLYING}$ during AF prior to activating ventricular pacing (as in FIG. 3.) At step 300, upon detection of AF, the pacer/ICD delays activation of any ventricular pacing that might otherwise be immediately activated. The delay is typically for 5 to 10 seconds. During this delay, at step 302, the pacer/ICD detects intrinsic ventricular beats on a ventricular sensing channel and then determines $VR_{UNDERLYING}$ by measuring intervals between the detected intrinsic ventricular beats and averaging those intervals. At step 304, the pacer/ICD then sets $VR_{MAX}=VR_{UNDERLYING}+VR_{MAX-INCREASE}$.

Figure 6:
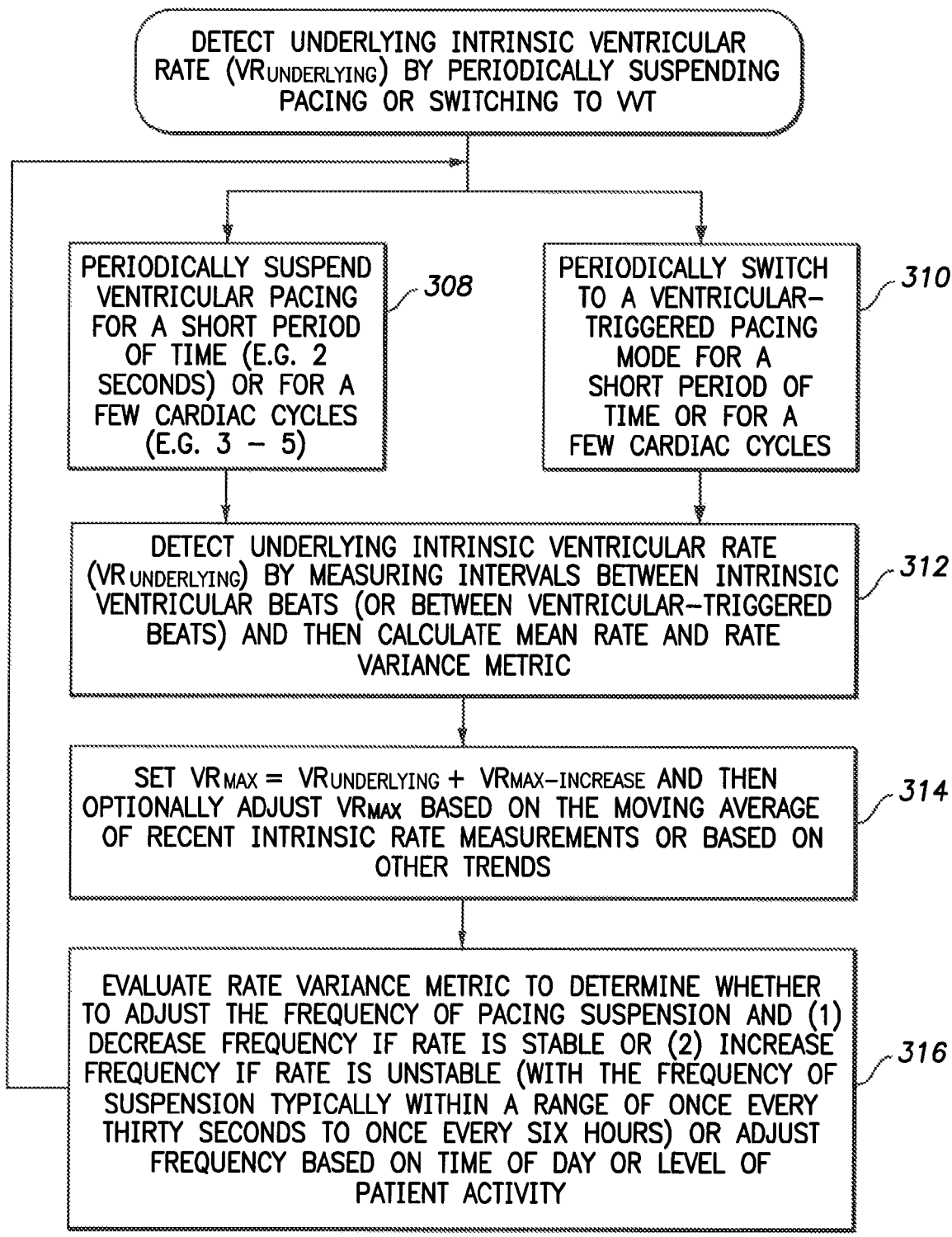
FIG. 6 illustrates another exemplary technique for detecting $VR_{UNDERLYING}$ for use with the procedure of FIG. 4, wherein $VR_{UNDERLYING}$ is determined during AF by periodically suspending ventricular pacing or by periodically switching to VVT pacing.

FIG. 6 illustrates exemplary techniques for use at step 204 of FIG. 4 for determining $VR_{UNDERLYING}$ by periodically suspending on-going pacing or by periodically switching from an asynchronous pacing mode to VVT. At step 308, the pacer/ICD monitors an internal timer and periodically suspends any on-going ventricular pacing for a short period of time (e.g. 2 seconds) or for a few cardiac cycles (e.g. 3-5.) The duration of time during which pacing is suspended and/or the number of cardiac cycles during which pacing is suspended are preferably both programmable by the clinician. The initial frequency at which pacing suspension occurs is also preferably programmable. In some examples, the frequency is programmed (and restricted) within the range of 30 seconds to 6 hours. Still further, whether the pacer/ICD suspends pacing or switches to VVT is likewise programmable by the clinician.

Alternatively, at step 310, the pacer/ICD periodically switches to VVT pacing for a short period of time (e.g. 2 seconds) or for a few cardiac cycles (e.g. 3-5.) With VVT, intrinsic ventricular beats (i.e. QRS-complexes) are detected and, upon detection, a V-pulse is immediately delivered. VVT is employed at step 310 is an effort to improve hemodynamics (as least as compared to implementations wherein pacing is suspended.) Again, the duration of time during which pacing is switched and/or the number of cardiac cycles during which pacing is switched are preferably both programmable by the clinician. The initial frequency at which switched occurs is also preferably programmable.

Thereafter, while pacing is suspended or VVT is activated, the pacer/ICD at step 312 detects the underlying intrinsic ventricular rate ($VR_{UNDERLYING}$) by detecting and measuring the intervals between intrinsic ventricular beats sensed on the ventricular sensing channel. The pacer/ICD also preferably calculates a mean ventricular rate and a rate variance metric using otherwise conventional techniques. At step 314, the pacer/CD sets $VR_{MAX}=VR_{UNDERLYING}+VR_{MAX-INCREASE}$ and then optionally adjusts $VR_{MAX}$ based on moving average of recent intrinsic rate measurements or based on other trends. That is, trends in recently detected values for $VR_{UNDERLYING}$ may be exploited to set $VR_{MAX}$. This may be particularly useful if a strong trend in $VR_{UNDERLYING}$ values is detected.

At step 316, the pacer/ICD evaluates a rate variance metric to determine whether to adjust the frequency of pacing suspension (or VVT activation) and (1) lowers the frequency if the rate is relatively stable or (2) increases the frequency if rate is relatively unstable. According to the preferred method, the rate variance metric is the variance of the means of several (e.g. 5) prior periodic rate samples. In another example, the rate variance metric is an average of the variances calculated as described for several prior periodic rate samples. As noted, the frequency of suspension is typically restricted within the range of once every 30 seconds to once every six hours. In one example, the frequency is initially set to once every 30 seconds. If, after a week of operation, the rate variance metric is found to be low (i.e. below a predetermined variance threshold), the frequency at which $VR_{UNDERLYING}$ is detected is changed to once every 60 seconds. Further adjustments may be made each subsequent week depending upon the value of the rate variance metric and on any trends detected therein. (In this regard, note that, within some patients, episodes of AF can last well over a week. Indeed, within some patients, particularly the elderly, AF can occur more or less continuously without abating. That is, individual "episodes" of AF can last for months or years.) Rate variance data and trend data may also be stored for clinician review or for diagnostic purposes.

Additionally, or alternatively, at step 316, the frequency at which $VR_{UNDERLYING}$ is detected is adjusted based on time of day or the level of patient activity as detected by the device by an activity sensor. For example, $VR_{UNDERLYING}$ can be detected more frequently during the day and while the patient is active than at night while the patient is asleep.

Steps 308-316 are repeated so as to periodically update the value for $VR_{MAX}$ so that the updated value can be used to control and limit the ventricular pacing rate during AF. In some implementations, if a relatively long period of time (e.g. 30 minutes) has occurred since the last measurement of $VR_{UNDERLYING}$, the value for $VR_{MAX}$ to be used can be adjusted based on any on-going trends in $VR_{UNDERLYING}$ without necessarily detecting new values of $VR_{UNDERLYING}$.

Figure 7:
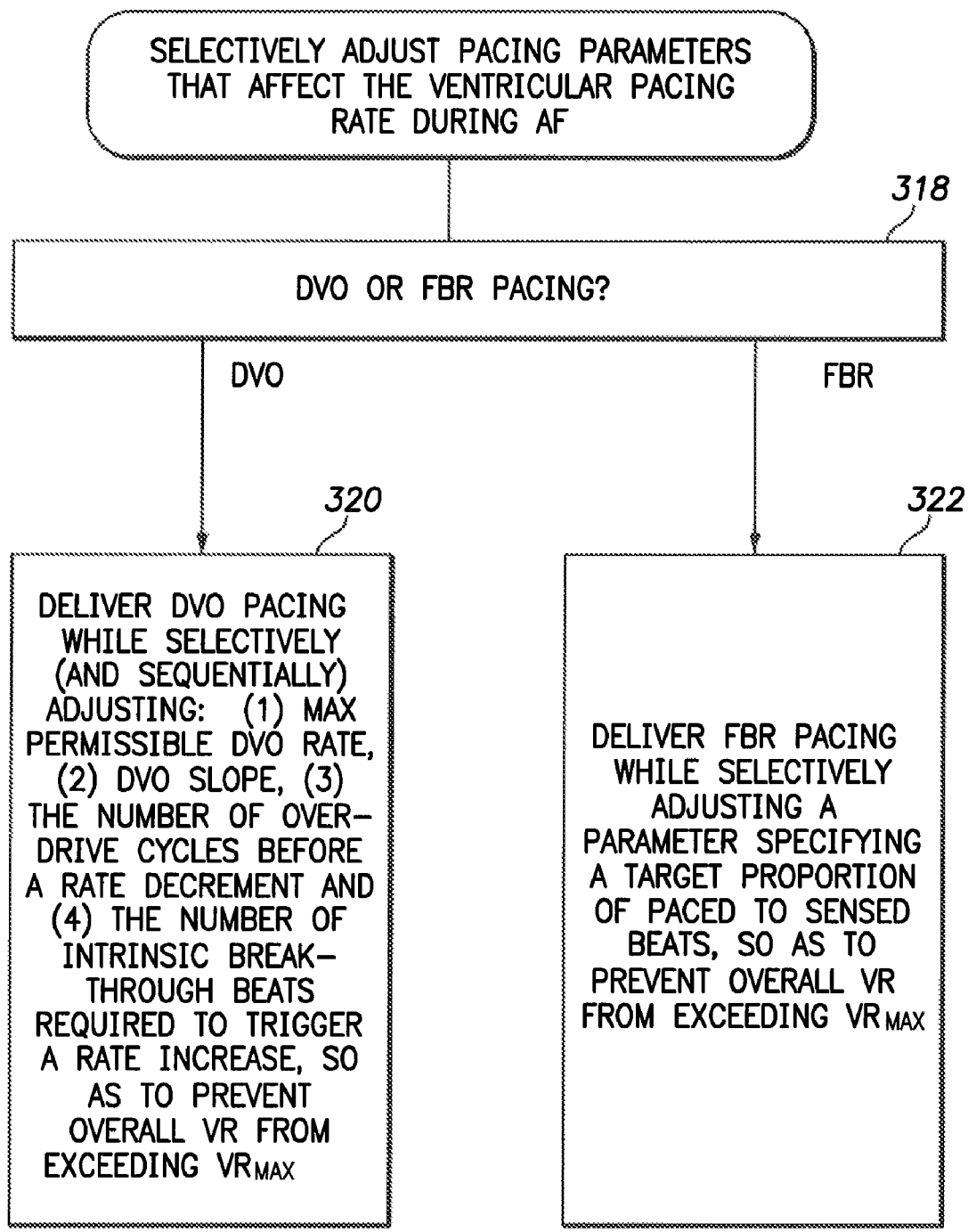
FIG. 7 illustrates an exemplary technique for selectively adjusting DVO or FBR pacing parameters that affect the ventricular pacing rate during AF so as to keep the rate below $VR_{MAX}$, which may be employed during AF in accordance with the procedures of FIG. 4.

FIG. 7 illustrates exemplary techniques for use at step 208 of FIG. 4 for selectively adjusting pacing parameters that affect the ventricular pacing rate during an episode of AF. That is, once ventricular pacing is activated during an episode of AF, these techniques are exploited to adjust the ventricular pacing to keep the paced ventricular rate below $VR_{MAX}$. In this particular example, the ventricular pacing applied during AF is either DVO or FBR pacing, though other ventricular pacing procedures can instead be used where appropriate. At step 318, upon detection of AF, the pacer/ICD determines whether to deliver DVO or FBR pacing. This determination is made based on pre-programming provided by the clinician and by the capabilities of the device.

If DVO, then, at step 320, the pacer/ICD delivers DVO pacing while selectively (and sequentially) adjusting: (1) the maximum allowed pacing rate during DVO, (2) the DVO slope, (3) the number of overdrive cycles before a rate decrease (i.e. the dwell time) and (4) the number of intrinsic ventricular breakthrough beats required to trigger a rate increase (N), or other suitable DVO parameters, so as to prevent the overall VR—representative of both paced and intrinsic ventricular beats—from exceeding $VR_{MAX}$. By "sequentially," it is meant that these parameters are adjusted in the order listed. That is, the maximum allowed pacing rate during DVO is adjusted first, then if necessary the slope is adjusted, then the dwell time is adjusted, and then if necessary N is adjusted. These or similar DVO parameters are discussed in U.S. Pat. No. 7,308,306 (cited above) or in other patents and publications pertaining to overdrive pacing. Note that, herein, "breakthrough" beats are any intrinsic ventricular beats detected during ventricular pacing. Note also that, even though the pacing rate may be limited to $VR_{MAX}$, the average ventricular rate can still be greater than $VR_{MAX}$ because of breakthrough beats. However, it is also desirable to allow the pacing control algorithm of the device to operate below this ceiling to the greatest extent possible. Therefore, the max DVO rate should be the first DVO parameter adjusted, but the max DVO rate should not be set to less than $VR_{MAX}$. In one particular example, DVO is performed as follows:

1. Detect a breakthrough ventricular beat (i.e. a QRS-complex) on a ventricular sensing channel.
2. If "N" additional QRS-complexes (i.e. ventricular breakthrough beats) are sensed within $X_{VENT}$. ventricular cycles (or within $X_{VENT}$. amount of time), increase the ventricular pacing rate (VR) by $Y_{VENT}$. ppm.
   a) $X_{VENT}$. is typically programmable from about 20 to 60 ventricular cycles.
   b) $Y_{VENT}$. (which is the "rate increment" or the "slope") is the programmable rate increase and is typically programmable from 2-25 ppm.
   c) N (which relates to the number of intrinsic breakthrough beats required to trigger a rate increase) is typically programmable from 1 to 5. (For example, with N=1, two ventricular breakthrough beats can trigger a rate increase; with N=2, three ventricular breakthrough beats can trigger a rate increase, etc.)
3. If $Z_{VENT}$. ventricular cycles occur without a ventricular rate increase, then decrease ventricular rate by W ppm/cardiac cycle.
   a) $Z_{VENT}$. (which is the "dwell time") represents the amount of time before the ventricular pacing rate is decreased and is programmable from 20 to 60 ventricular cycles.
   b) $W_{VENT}$. (which is the "recovery rate") is programmable at 1, 2, 3, 4, or 5 ppm/cardiac cycle.
4. Maintain the ventricular pacing rate at or below the predetermined maximum DVO rate.

Hence, in this example, any of the maximum DVO rate, N, $X_{VENT}$., $Y_{VENT}$. (i.e. slope), $Z_{VENT}$. (i.e. dwell time), and $W_{VENT}$. (i.e. "recovery rate") can be adjusted by the pacer/ICD to keep the paced ventricular rate below $VR_{MAX}$. That is, in use, the pacer/ICD monitors the ventricular pacing rate and selectively adjusts these DVO control parameters to keep the overall ventricular rate below $VR_{MAX}$. In one particular example, should a DVO rate increment specified by the above algorithm cause the overall ventricular rate to exceed $VR_{MAX}$, the rate increment is not applied. Preferably, the parameters are adjusted so as to also minimize the mean ventricular rate, while also achieving (if possible within the patient) a targeted proportion of paced beats to sensed beats or a predetermined degree of ventricular smoothness. Otherwise conventional adaptive pacing parameter adjustment techniques may be employed to adjust the parameters within certain predetermined acceptable ranges so as to meet these or other goals. U.S. Pat. No. 7,308,306 also discusses adaptive techniques for automatically varying ventricular overdrive pacing control parameters so as to achieve a target degree of smoothing of the ventricular rate or a target percentage of ventricular overdrive paced beats.

Note that the aforementioned "slope" can also be defined in terms of one or more overdrive pacing response functions pre-programmed into the pacer/ICD. Each pacing response function specifies an overdrive ventricular pacing rate for each corresponding intrinsic ventricular rate throughout a broad range of detectable ventricular rates. The use of pacing response functions to specify slope is discussed in connection with atrial overdrive pacing in U.S. Published Patent Application 2003/0130704, of Florio et al., entitled "Method and Apparatus for Dynamically Adjusting a Non-Linear Overdrive Pacing Response Function", filed Jan. 9, 2002. See also 2003/0130703, of Florio et al., entitled "Method and Apparatus for Dynamically Adjusting Overdrive Pacing Parameters," filed Jan. 9, 2002. These techniques, although described with reference to controlling DAO can be selectively adapted to control DVO, where appropriate.

Still further, note that with DVO the ventricular overdrive rate need not be faster than the intrinsic ventricular rate that would otherwise occur, i.e. "overdrive" pacing in the ventricles can be used to reduce the ventricular rate (i.e. to "underdrive" the ventricles). Accordingly, as the term is used herein, DVO generally refers to a dynamic ventricular overdrive/underdrive pacing procedure, i.e. DVO refers to a pacing procedure wherein pacing is delivered at a rate selected to permit detection of at least some intrinsic ventricular beats and wherein the ventricular rate is automatically and selectively controlled in response to the detected intrinsic ventricular beats to overdrive or underdrive the ventricles.

If FBR pacing has instead been selected at step 318, then, at step 322, the pacer/ICD delivers FBR pacing while adjusting a target proportion or ratio (R) of paced to sensed beats, so as to prevent VR from exceeding $VR_{MAX}$. In other examples, the FBR controller of the pacer/ICD may additionally allow for controlling other FBR pacing parameters such as: (1) an amount of pacing rate increase (M), which can be specified in ppm or as a percentage increase and (2) an amount of time that a n MSBR value is used following detection of AF (e.g., X minutes). These or similar FBR control parameters are discussed in U.S. Pat. No. 7,187,972 (cited above) or in other patents and publications pertaining to FBR pacing.

As mentioned above, FBR pacing seeks to maintain a high percentage of ventricular paced beats during AF. Monitoring is performed to determine whether pacing in accordance with the MSBR satisfies a MAPC value. The MSBR is increased and pacing is performed in accordance with the increased MSBR, when the MAPC is not satisfied. The MSBR is periodically decreased and pacing is performed in accordance with the decreased MSBR when the MAPC is satisfied. FBR pacing is particularly well-suited for use in heart failure patients receiving CRT, which seeks to resynchronize the ventricles while achieving a high percentage of paced ventricular beats.

More specifically, as described in U.S. Pat. No. 7,187,972, the MSBR is kept high enough so that biventricular pacing generally occurs at least a minimum acceptable amount, specified by the MAPC. In one particular example, the MAPC is defined as a pacing percentage or as an "X out of Y" criterion. For example, the MAPC can specify that 90% of all ventricular beats should be paced, or that 9 out of 10 ventricular beats should be paced. If the MAPC is not met or exceeded, the pacer/ICD determines whether the MSBR is at a maximum programmed MSBR value. If the MSBR is at its maximum, then there are no further rate increases. However, if MSBR is not at its maximum, then the MSBR is increased (in an attempt to increase the MSBR above the intrinsic rate of the ventricles so that the MAPC can be met). In one example, the increase is by a fixed amount, e.g., by M ppm. In another embodiment, the increase is by a percentage (e.g., 2%). In still another example, the increase of the MSBR is accomplished by a reduction in the intervals between beats (e.g., by reducing the interval between consecutive beats by N msec).

If the MAPC is met or exceeded, then the pacer/ICD determines of whether the MSBR has been at its current value for at least a specified period of time (e.g., X minutes). If not, the MSBR is maintained at its current value, and the pacer/ICD continues to monitor for AF. If the MSBR has been at its current value for at least the specified predetermined period of time (e.g., X minutes), then the MSBR is decreased. The decrease can be, e.g., by a fixed amount, by a percentage, or by an increase in the interval between beats. Such a decrease increment can be the same as, or different than, the increase increment used when increasing the rate. The MSBR should not be decreased such that it is less than a minimum programmed MSBR value. Further details of FBR pacing may be found within U.S. Pat. No. 7,187,972.

As can be appreciated, depending upon the capabilities of the device, any of the various control parameters exploited by the FBR pacing technique can potentially be selectively and adaptively adjusted to maintain VR below $VR_{MAX}$ and to achieve other goals, such as reducing the mean ventricular rate or achieving some target proportion of paced to sensed ventricular beats.

What have been described are various techniques for controlling ventricular pacing during atrial tachyarrhythmias. Although described with reference to AF, the techniques of the invention may potentially also be applied, where appropriate, to controlling pacing parameters during other arrhythmias. Also, although particular pacing procedures have been described herein (DVO, FBR pacing, etc.), these are merely exemplary and other suitable pacing procedures may be exploited, where appropriate, either additionally or alternatively. Note also that DVO and FBR-pacing can potentially both be activated within a pacer/ICD at the same time and hence should not be seen as excluding one another. Also, in addition to specifying the $VR_{MAX-INCREASE}$ value (which is used to set a $VR_{MAX}$ value based on $VR_{UNDERLYING}$), the clinician may also be asked to specify an absolute maximum VR value, which can be used to override or limit $VR_{MAX}$. As can be appreciated, a wide range of options are available consistent with the general principles of the invention.

For the sake of completeness, a detailed description of an exemplary pacer/ICD for performing these techniques will now be provided. However, principles of invention may be implemented within other pacer/ICD implementations or within other implantable devices, including stand-alone CRT devices that do not provide full pacer/ICD functionality.

Exemplary Pacer/ICD

FIG. 8 provides a simplified block diagram of a pacer/ICD 10, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 10 is shown in electrical communication with a heart 412 by way of a left atrial lead 420 having an atrial tip electrode 422 and an atrial ring electrode 423 implanted in the atrial appendage. Pacer/ICD 10 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 10 is coupled to a "coronary sinus" lead 424 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus. Accordingly, an exemplary coronary sinus lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 8, it should also be understood that additional stimulation leads (with one or more pacing, sensing and/or shocking electrodes) may be used in order to efficiently and effectively provide pacing stimulation to the left side of the heart or atrial cardioversion and/or defibrillation.

Figure 9:
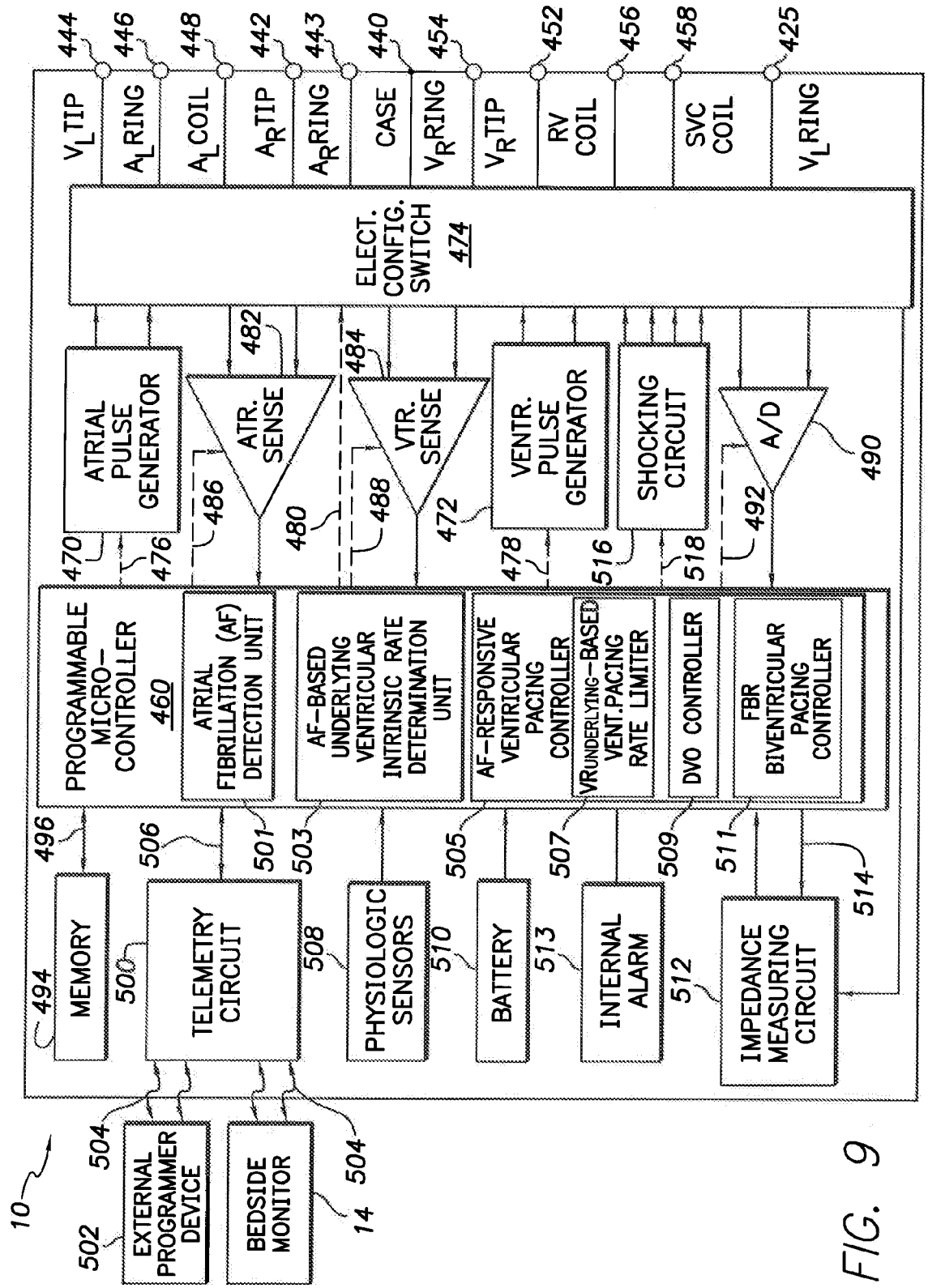
FIG. 9 is a functional block diagram of the pacer/ICD of FIG. 8, illustrating basic circuit elements that provide cardioversion, defibrillation and/or pacing stimulation in four chambers of the heart and particularly illustrating components for determining $VR_{UNDERLYING}$ and for controlling ventricular pacing during AF based, in part, on $VR_{UNDERLYING}$.

A simplified block diagram of internal components of pacer/ICD 10 is shown in FIG. 9. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 440 for pacer/ICD 10, shown schematically in FIG. 9, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal ($A_R$ TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial ring electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($R_V$ COIL) 456, and an SVC shocking terminal (SVC COIL) 458, which are adapted for connection to the right ventricular tip electrode 432, right ventricular ring electrode 434, the RV coil electrode 436, and the SVC coil electrode 438, respectively.

At the core of pacer/ICD 10 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 9, an atrial pulse generator 470 and a ventricular pulse generator 472 generate pacing stimulation pulses for delivery by the right atrial lead 420, the right ventricular lead 430, and/or the coronary sinus lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry 479 used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art.

Atrial sensing circuits 482 and ventricular sensing circuits 484 may also be selectively coupled to the right atrial lead 420, coronary sinus lead 424, and the right ventricular lead 430, through the switch 474 for detecting the presence of cardiac activity in each of the four chambers of the heart.

Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 10 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 10 utilizes the atrial and ventricular sensing circuits, 482 and 484, to sense cardiac signals to determine whether a rhythm is physiologic or pathologic. As used in this section, "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the coronary sinus lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 10 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 10 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 10 (as contained in the microcontroller 460 or memory 494) to be sent to the external device 502 through an established communication link 504. Pacer/ICD 10 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep.

Accordingly, the microcontroller 460 responds by adjusting the various pacing parameters (such as rate, AV/PV delay, V-V Delay, etc.) at which the atrial and ventricular pulse generators, 470 and 472, generate stimulation pulses. While shown as being included within pacer/ICD 10, it is to be understood that the physiologic sensor 508 may also be external to pacer/ICD 10, yet still be implanted within or carried by the patient. A common type of rate responsive sensor is an activity sensor incorporating an accelerometer or a piezoelectric crystal, which is mounted within the housing 440 of pacer/ICD 10. Other types of physiologic sensors are also known, for example, sensors that sense the oxygen content of blood, respiration rate and/or minute ventilation, pH of blood, ventricular gradient, etc.

Insofar as controlling ventricular pacing during AF is concerned, the microcontroller includes an AF detection unit 501 and an AF-based underlying intrinsic ventricular rate determination unit 503, which is operative to detect $VR_{UNDERLYING}$ during AF. An AF-responsive ventricular pacing controller 505 controls ventricular pacing during AF. During an episode of AF, controller 505 is operative to deliver ventricular pacing at a ventricular rate not exceeding a $VR_{MAX}$ value set based on the $VR_{UNDERLYING}$ and a $VR_{MAX\text{-}INCREASE}$ value retrieved from memory 494. To this end, controller 505 includes a $VR_{UNDERLYING}$-based ventricular pacing rate limiter unit 507, which is operative to adaptively adjust pacing control parameters to keep the ventricular pacing rate at or below a $VR_{MAX}$ value set based on $VR_{UNDERLYING}$ (as described above.) Controller 505 also includes a DVO controller 509 and an FBR pacing controller 511 to control (respectively) DVO and FBR pacing. Although shown as being part of the microcontroller, the various units of the microcontroller can instead be implemented as components separate from the microcontroller.

An internal alarm 513 is provided to deliver any necessary warning signals to the patient via, for example, vibration or via "tickle" voltages. Such warnings may be appropriate if, due to device malfunction or for other reasons, the pacer/ICD is unable to keep the ventricular rate below $VR_{MAX}$ during AF.

The pacer/ICD additionally includes a battery 510, which provides operating power to all of the circuits shown in FIG. 9. The battery 510 may vary depending on the capabilities of pacer/ICD 10. If the system only provides low voltage therapy, a lithium iodine or lithium copper fluoride cell may be utilized. For pacer/ICD 10, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 10 is preferably capable of high voltage therapy and appropriate batteries.

As further shown in FIG. 9, pacer/ICD 10 is shown as having an impedance measuring circuit 512 which is enabled by the microcontroller 460 via a control signal 514. Exemplary uses for an impedance measuring circuit include, but are not limited to: lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 512 is advantageously coupled to the switch 474 so that any desired electrode may be used.

In the case where pacer/ICD 10 is intended to operate as an implantable cardioverter/defibrillator (ICD) device, it detects the occurrence of an arrhythmia, and, if so programmed, automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode).

Preferably, during AF, DVO or FBR pacing is performed, as discussed above. Should a cardioversion shock be desired, perhaps because AF does not terminate within an acceptable period of time, the device deactivates any DVO or FBR pacing and instead delivers the cardioversion shock. Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

What have been described are various techniques for controlling ventricular pacing during AF. Although described primarily with reference to an example wherein the implanted device is an ICD, principles of the invention are applicable to other implanted cardiac stimulation devices as well such as pacemakers without defibrillation capability. The various functional components of the exemplary systems may be implemented using any appropriate technology including, for example, microprocessors running software programs or application specific integrated circuits (ASICs) executing hard-wired logic operations. The exemplary embodiments of the invention described herein are merely illustrative of the invention and should not be construed as limiting the scope of the invention.

What is claimed is:

1. A method for use by an implantable medical device equipped to selectively deliver pacing therapy to the ventricles during atrial fibrillation (AF), comprising:
    inputting a maximum ventricular rate increase;
    detecting AF within the heart of a patient in which the device is implanted;
    determining an underlying intrinsic ventricular rate during AF; and
    delivering ventricular pacing therapy during AF at a ventricular rate not exceeding a maximum rate set based on the underlying intrinsic ventricular rate and the maximum rate increase.

2. The method of claim 1 wherein delivering ventricular pacing therapy during AF is performed to maintain an overall ventricular rate representative of both paced beats and intrinsic beats below the maximum rate.

3. The method of claim 1 wherein the maximum rate increase is a user-specified value initially received from an external programmer device.

4. The method of claim 1 wherein the maximum rate increase is determined by the implantable device.

5. The method of claim 1 wherein determining the underlying intrinsic ventricular rate during AF includes:
    detecting ventricular intrinsic beats prior to activation of ventricular pacing during AF; and
    determining the underlying intrinsic ventricular rate based on the intrinsic beats detected prior to the activation of ventricular pacing.

6. The method of claim 5 wherein detecting ventricular intrinsic beats prior to activation of ventricular pacing during AF is performed for a period of time in the range of 3 to 120 seconds.

7. The method of claim 1 wherein determining the underlying intrinsic ventricular rate during AF includes:
    temporarily suspending any on-going ventricular pacing delivered during AF; and
    determining the underlying intrinsic ventricular rate based on intrinsic beats detected during the suspension of ventricular pacing.

8. The method of claim 7 wherein temporarily suspending ventricular pacing during AF is performed for one of: a predetermined number of pacing cycles or a predetermined number of seconds.

9. The method of claim 7 wherein temporarily suspending ventricular pacing during AF is performed periodically.

10. The method of claim 7 wherein the underlying intrinsic ventricular rate is determined during AF based on trends derived from previously-detected underlying intrinsic ventricular rates.

11. The method of claim 10 wherein the underlying intrinsic ventricular rate is determined during AF based on a moving average derived from previously-detected underlying intrinsic ventricular rates.

12. The method of claim 1 wherein the device is equipped to deliver pacing in a ventricular-triggered pacing mode and wherein determining the underlying intrinsic ventricular rate includes:
    temporarily switching to the ventricular-triggered pacing mode; and
    determining the underlying intrinsic ventricular rate during AF based on intrinsic beats detected during ventricular-triggered pacing.

13. The method of claim 1 wherein delivering ventricular pacing therapy during AF at a ventricular rate not exceeding the maximum rate is achieved by selectively adjusting parameters affecting the ventricular pacing rate used by the implantable device.

14. The method of claim 13 wherein the implantable device is equipped to deliver dynamic ventricular overdrive (DVO) pacing and wherein selectively adjusting parameters affecting the ventricular pacing rate during AF includes selectively adjusting one or more DVO control parameters.

15. The method of claim 1 wherein the maximum rate is set equal to the underlying intrinsic ventricular rate plus the maximum rate increase.

16. A system for use with an implantable medical device equipped to selectively deliver pacing therapy to the ventricles, comprising:
   an atrial fibrillation (AF) detection unit;
   an AF-based underlying intrinsic ventricular rate determination unit; and
   an AF-responsive ventricular pacing controller operative during AF to deliver ventricular pacing at a ventricular rate not exceeding a maximum rate set based on the underlying intrinsic ventricular rate and a maximum rate increase.

17. The system of claim 16 wherein the AF-responsive ventricular pacing controller is operative to maintain an overall ventricular rate representative of both paced beats and intrinsic beats below the maximum rate.

18. The system of claim 16 wherein the AF-responsive ventricular pacing controller includes an underlying intrinsic ventricular rate ($VR_{UNDERLYING}$)-based ventricular pacing rate limiter operative to limit the ventricular rate during AF to a maximum ventricular rate ($VR_{MAX}$) set based on $VR_{UNDERLYING}$ and a maximum rate increase ($VR_{MAX\text{-}INCREASE}$).

19. A system for use with an implantable medical device equipped to selectively deliver pacing therapy to the ventricles during an episode of atrial fibrillation (AF), comprising:
   means for detecting AF;
   means for determining an underlying intrinsic ventricular rate during AF; and
   means for delivering ventricular pacing therapy during AF at a ventricular rate not exceeding a maximum rate set based on the underlying intrinsic ventricular rate and a maximum rate increase.

20. The system of claim 19 wherein the means delivering ventricular pacing therapy during AF is operative to maintain an overall ventricular rate representative of both paced beats and intrinsic beats below the maximum rate.

* * * * *